United States Patent [19]

Maki et al.

[11] Patent Number: 4,791,235
[45] Date of Patent: Dec. 13, 1988

[54] PROCESS FOR SEPARATING 2,6-DIMETHYLNAPHTHALENE

[75] Inventors: Takao Maki, Fujisawa; Toshiharu Yokoyama; Akio Nakanishi, both of Machida; Katashi Shioda, Hadano; Haruki Asatani, Yokohama, all of Japan

[73] Assignee: Mitsubishi Chemical Industries Limited, Japan

[21] Appl. No.: 126,417

[22] Filed: Nov. 30, 1987

[30] Foreign Application Priority Data

Nov. 28, 1986 [JP] Japan .................................. 61-283547
Dec. 11, 1986 [JP] Japan .................................. 61-295589

[51] Int. Cl.$^4$ .................................................. C07C 7/00
[52] U.S. Cl. ............................... 585/806; 585/812; 585/828; 585/831
[58] Field of Search ............... 585/804, 806, 812, 828, 585/831

[56] References Cited

U.S. PATENT DOCUMENTS

| | | | |
|---|---|---|---|
| 3,235,615 | 2/1966 | Allen et al. ........................... | 585/806 |
| 3,772,399 | 11/1973 | Hedge et al. . | |
| 3,798,280 | 3/1974 | Shimado et al. ...................... | 585/806 |
| 3,957,896 | 5/1976 | Yokoyama et al. ................... | 585/901 |

FOREIGN PATENT DOCUMENTS

| | | | |
|---|---|---|---|
| 496433 | 9/1953 | Canada ................................ | 585/806 |
| 730740 | 3/1966 | Canada ................................ | 585/812 |
| 3531559 | 3/1987 | Fed. Rep. of Germany ...... | 585/813 |
| 1333264 | 1/1970 | United Kingdom . | |
| 1426924 | 6/1972 | United Kingdom . | |

Primary Examiner—Curtis R. Davis
Attorney, Agent, or Firm—Jordan B. Bierman

[57] ABSTRACT

A method of separating 2,6-dimethylnaphthalene from a feed material containing a mixture of dimethylnaphthalene isomers comprises the steps of:

adsorption separation using an adsorbent of a zeolite Y containing alkali metal or zinc and a desorbent of an organic solvent mainly composed of paraxylene and/or orthoxylene to obtain a solution consisting of the desorbent and the feed material containing 2,6-dimethylnaphthalene at a concentration of at least 60 wt % on the feed material other than desorbent; and crystallization of the solution having a concentration of the desorbent at 30 to 90 wt % to obtain 2,6-dimethylnaphthalene of high purity in a crystalline form.

14 Claims, 1 Drawing Sheet

PROCESS FOR SEPARATING 2,6-DIMETHYLNAPHTHALENE

BACKGROUND OF THE INVENTION

The present invention relates to a method of separating 2,6-dimethylnaphthalene from a feed material containing a mixture of dimethylnaphthalene isomers (the term "dimethylnaphthalene" is hereinafter referred to as DMN). More particularly, the present invention relates to a method of selective adsorption and desorption of 2,6-DMN which employs a specified solid adsorbent in combination with a specified desorbent followed by crystallization with said desorbent in order to separate 2,6-DMN from a stream of feed material containing 2,6-DMN and at least one other DMN isomer.

A purity of 2,6-DMN hereinafter mentioned means a value obtained by dividing a weight of 2,6-DMN in a unit volume by a weight of feed material containing no desorbent in the unit volume.

It has been recognized in the prior art that a zeolite X or Y containing a certain species of cations on ion-exchangeable cation sites can be employed to separate a particular DMN isomer from a mixture containing other isomers. See, for example, U.S. Pat. Nos. 3,133,126 and 3,114,782 which show that a zeolite X containing sodium or calcium on ion-exchangeable cation sites is useful as an adsorbent for effectively selective adsorption of one DMN isomer from another.

Japanese patent publication No. 945/1977 shows that 2,7-DMN can be selectively separated from an eutectic mixture of 2,6-DMN and 2,7-DMN using zeolite Y, with benzene, toluene or ortho xylene being used as a desorbent.

Japanese patent publication No. 27578/1974 shows that 2,6-DMN can be separated from other isomers using zeolite Y. Dutch Pat. No. 7307794, U.S. Pat. Nos. 3,772,399, 3,840,610, 3,895,080, 4,014,949, etc., show that zeolite Y is useful as an adsorbent in separating cyclic hydrocarbons.

However, concerning the selective adsorption of one DMN isomer from another, U.S. Pat. Nos. 3,133,126 and 3,114,782 merely present a batch method for dilute solution of a mixture of DMN isomers in a container in the presence of paraffin which is not substantially involved in the actual case of adsorption. These patents do not make any mention of the participation of desorbents which are indispensable to commercial operations of selective adsorption process, such as continuous separation of DMN isomers using simulated moving beds, etc.

The disclosure of desorbents which are necessary for commercial operations of selective adsorption of DMN isomers also lacks from Japanese patent publication No. 27578/1974, U.S. Pat. Nos. 3,772,399, 3,895,080, 4,014,949, and Dutch Pat. No. 7307794. In general, in order to ensure successful operations of adsorption separation, the system to be employed must satisfy the following requirements for an adsorbent and a desorbent: as for the adsorbent, it must offer a high separation factor, causes no deterioration of the substances to be processed, and allows for rapid adsorption and desorption of said substances; as for the desorbent, it must be capable of promoting the adsorption and desorption of the substances being processed. If these requirements are not satisfied, problems such as increased tailings of the processed substances occur and the substance of interest cannot be separated with high efficiency.

The technique shown in Japanese patent publication No. 945/1977 is somewhat advanced in that it proposes the use of an adsorbent in combination with a desorbent. However, this reference suggests nothing about a specific method for selectively separating a desired isomer of high purity from the eutectic mixture obtained.

The following methods could be employed to further enrich a certain DMN isomer which is obtained by adsorption separation:

(1) the mixture is added in an appropriate solvent and the solution is repeatedly subjected to the same operations of adsorption and desorption;

(2) the mixture is crystallized in a lower aliphatic alcohol such as methanol in accordance with the method disclosed in Japanese patent publication No. 24505/1976 or 34695/1972; and (3) the mixture is subjected to "solvent-free crystallization" in accordance with the method disclosed in Japanese patent publication No. 27578/1974.

However, the first of these methods has the disadvantage that since impurities having aromatic rings that are inseparable from 2,6-DMN by this method are present in small amount in the feed, it is impossible to separate 2,6-DMN in a purity of, for example, 99% and higher, even if repeated cycles of adsorption and desorption are performed. This method is also economically disadvantageous and is not suitable for use in commercial operations since it requires a large quantity of desorbent (a desorbent is necessary for each cycle of adsorption and desorption) and because the used desorbent must be recovered from the system in subsequent processing. The second method is not necessarily advantageous, either, because the solubility of DMN isomers in lower aliphatic alcohols such as methanol is so low that when the raffinate, or residual components other than 2,6-DMN that are present in the mother liquor for crystallization, is transferred to a subsequent step, a large quantity of a lower aliphatic alcohol must be accompanied. The third method is capable of yielding a desired substance in high purity but this involves eutectic problems and hence is not advantageous with respect to high recovery. Furthermore, this is not adapted to continuous operations and hence is not advantageous for commercial application.

The present inventors conducted intensive studies in order to solve the aforementioned problems of the prior art techniques and found that when a zeolite Y containing specific metallic ions was used as an adsorbent in combination with a specified desorbent, efficient adsorption separation of 2,6-DMN could be accomplished. The present inventors also found that 2,6-DMN of high purity could be obtained in high yield by subsequently performing crystallization under specified conditions using said desorbent. The present invention has been accomplished on the basis of these findings.

SUMMARY OF THE INVENTION

An object, therefore, of the present invention is to provide a commercially advantageous method of separating a high purity form of 2,6-DMN in high yield from a feed material containing a mixture of DMN isomers.

This object of the present invention can be easily attained by a method for separating 2,6-DMN from a feed material containing a mixture of DMN isomers comprises the steps of:

adsorption separation using an adsorbent of a zeolite Y containing an alkali metal or zinc and a desorbent of an organic solvent mainly composed of paraxylene and/or orthoxylene to obtain a solution consisting of the desorbent and the feed material containing 2,6-dimethylnaphthalene at a concentration of at least 60 wt% on said feed material except desorbent; and crystallization of said solution having a concentration of said desorbent at 30 to 90 wt% to obtain 2,6-dimethylnaphthalene of high purity in a crystalline form.

DETAILED DESCRIPTION OF THE INVENTION

Figure 1:
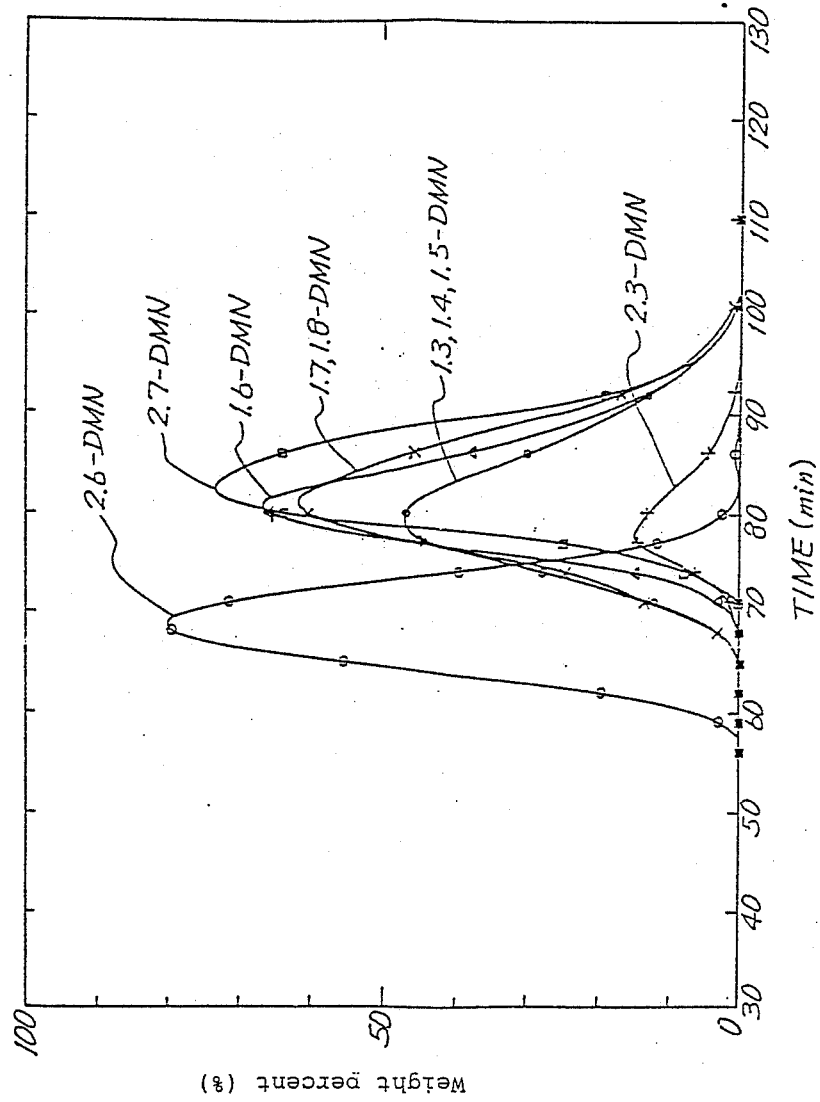

Many types of zeolite, both naturally occurring and artificially synthesized, are known in the art. However, not all of the known types of zeolite are effective as adsorbents for separating 2,6-DMN by the method of the present invention. Zeolite Y is employed in the present invention. Zeolite Y with a faujasite framework can be described as a mixture of oxides and expressed in terms of the molar ratios of oxides with respect to a sodium form by the following formula:

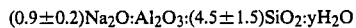

$(0.9\pm0.2)Na_2O:Al_2O_3:(4.5\pm1.5)SiO_2:yH_2O$ where y is of any value not exceeding 9 including zero.

It is important for the purposes of the present invention that a zeolite Y containing metals are effective these metal elements which include zinc and alkali metals such as lithium, sodium, potassium, rubidium and cesium, and lithium being particularly preferred.

In accordance with the method of the present invention, 2,6-DMN can be separated by employing a continuous separation technique such as elution type chromatography or simulated moving-bed chromatographic separation, in which a stream of feed material containing a mixture of DMN isomers is brought into contact with the zeolite Y characterized above which may be packed as a single bed in a chromatographic column and a desorptive material that is capable of selective desorption of 2,6-DMN is subsequently passed through this bed.

The zeolite used as an adsorbent is not limited to a powder form; it may be shaped into other forms such as pellets, extrudates, and granules. In the latter case, a binder such as silica, alumina or clay is incorporated in the zeolite and any suitable binder material may be employed. The zeolite which is to be packed in a column may assume any shape such as the form of spherical particles or crushed particles. If the average diameter of zeolite particles is written as d and the inside diameter of the column to be filled with the particles as D, the ratio of D/d is preferably at least 15, more preferably at least 20.

The purposes of the present invention can satisfactorily be achieved even if the zeolite Y is singly used as an adsorbent. However, in order to achieve more effective separation of 2,6-DMN, this zeolite Y used as an adsorbent is preferably combined with a specified zeolite X. The zeolite X that may be employed in combination with the zeolite Y can be described as a mixture of oxides and expressed in terms of the molar ratio of oxides with respect to a sodium form by the following formula:

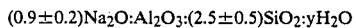

$(0.9\pm0.2)Na_2O:Al_2O_3:(2.5\pm0.5)SiO_2:yH_2O$ where y is of any value not exceeding 8 including zero.

As in the case of the zeolite Y, the zeolite X characterized above may have its cation sites ion-exchanged by any known method. For the purposes of the present invention, it is advantageous to use a zeolite X that contains an alkali metals such as lithium, sodium or potassium, preferably sodium. If the zeolite Y is to be used in combination with the zeolite X, various forms of combination may be employed; for instance, the two types of zeolite may be used in alternate layers as in the case where one type of zeolite is sandwiched between two layers of the other type of zeolite, or the two types of zeolite are packed in such a way that one type of zeolite is situated upstream whereas the other type of zeolite is situated downstream. Alternatively, the two types of zeolite may be mechanically mixed into a uniform blend.

In the most preferred embodiment of the present invention, the two types of adsorbent are arranged in such a way that the zeolite Y is situated upstream and the zeolite X situated downstream of a feed material stream containing a mixture of DMN isomers.

Choice of a suitable desorbent is another factor that is important for the purpose of achieving efficient adsorption separation of 2,6-DMN. The desorbent used in the present invention must be such that it is capable of selective and easy desorption of 2,6-DMN from the zeolite Y independently of any other components in the feed material, while it can be subsequently separated from 2,6-DMN by distillation or other techniques.

In the present invention, an organic solvent based on paraxylene and/or orthoxylene is used as a desorbent for effecting desorption of DMN. A mixture of paraxylene and/or orthoxylene and additives may also be used. The exemplary additives described above include saturated linear and/or branched hydrocarbons that are liquid under the conditions of operation employed, naphthenes which are saturated cyclic hydrocarbons with 3 to 20 carbon atoms that may have alkyl substituents, and aromatic hydrocarbons with 7 to 10 carbon atoms. More specific examples include: naphthenes such as cyclopropane, cyclobutane, cyclopentane, cyclohexane, cycloheptane, cyclooctane, cyclobutene, cyclopentene, cycloheptene, cyclooctene, cyclopentadiene, 1,3-cyclohexadiene, 1,4-cyclohexadiene, and cyclooctatetraene; saturated linear hydrocarbons such as n-pentane, n-hexane, n-heptane, n-octane, n-nonane and n-decane; and aromatic hydrocarbons such as toluene, m-xylene, ethylbenzene, n-propylbenzene, isopropylbenzene, 4-ethyltoluene, 3-ethyltoluene, 2-ethyltoluene, 1,2,4-trimethylbenzene, 1,3,5-trimethylbenzene, 1,2,3-trimethylbenzene, o-cymene, m-cymene, p-cymene, o-diethylbenzene, m-diethylbenzene, p-diethylbenzene, o-propyltoluene, m-propyltoluene, p-propyltoluene, n-butylbenzene, sec-butylbenzene, tert-butylbenzene, 1,2,3,4-tetramethylbenzene, and 1,2,3,5-tetramethylbenzene, 1,2,4,5-tetramethylbenzene, and 1,2,3,4-tetrahydronaphthalene. These compounds may be used either singly or in combination. Preferred among these compounds are toluene, m-xylene, ethylbenzene, n-propylbenzene, isopropylbenzene, 4-ethyltoluene, 1,2,4-trimethylbenzene, p-diethylbenzene, p-cymene and 1,2,3,4-tetrahydronaphthalene. Most preferred are toluene, ethylbenzene, isopropylbenzene, 4-ethyltoluene and 1,2,3,4-tetrahydronaphthalene.

These additives may be used in amounts of less than 40 wt% of the desorbent based on paraxylene and/or orthoxylene, namely, in such amounts that the concentration of paraxylene and/or orthoxylene is at least 60 wt%, preferably at least 70 wt%, of the total amount of the desorbent.

In accordance with the present invention, the combined use of the adsorbent and desorbent described above provides a solution consisting of the desorbent and a feed material containing 2,6-DMN at a concentration, i.e., purity, of at least 60 wt% on feed material other than desorbent. If the purity of 2,6-DMN is less than 60 wt%, 2,6-DMN cannot be obtained in high yield in a subsequent treatment of crystallization. Therefore, the purity of 2,6-DMN must be at least 60 wt%.

The so prepared solution is then, if necessary, conditioned to such a state that the concentration of the desorbent in the solution is in the range of 30 to 90 wt%. If the concentration of the desorbent in the solution exceeds 90 wt%, part thereof may be removed by a suitable means such as evaporation. If the concentration of the desorbent is less than 30 wt%, an additional amount of the desorbent may be added so that its concentration in the solution comes within the prescribed range. The solution containing the desorbent at a concentration of 30 to 90 wt% is subjected to a treatment of crystallization so as to recover a high purity of 2,6-DMN in high yield. Crystallization may be performed by various methods such as cooling the solution to a temperature at which the crystal of 2,6-DMN will form, or removing the desorbent by evaporation under vacuum, or crystallization in the presence of a diluent. In the last-mentioned method, a lower aliphatic alcohol such as methanol is usually employed as a diluent.

As described in detail on the foregoing pages, in accordance with the present invention, 2,6-DMN of high purity can be obtained in high yield by a two-stage process consisting of a step of adsorption separation employing a specified adsorbent in combination with a specified desorbent, and a step of crystallization in which the concentrated solution of 2,6-DMN prepared in the first step is conditioned for a specified composition and subjected to crystallization.

The operating conditions for establishing contact between the adsorbent and each of the feed and the desorbent should be appropriately selected in consideration of the physical properties of the feed and the desorbent, such as their melting point, boiling point and viscosity. In order to maintain a liquid state, the operating temperature is preferably adjusted to be within the range of 20° to 300° C., and the pressure in the range of substantially 1 to 50 atmospheres. More preferably, the temperature is selected from the range of 60° to 200° C., and the pressure from the range of substantially 1 to 20 atmospheres.

The feed to be processed by the method of the present invention is a feed material containing a mixture of DMN isomers. The term "a mixture of DMN isomers" means a mixture of 2,6-DMN and at least one other DMN isomer selected from among 2,7-DMN, 2,3-DMN, 1,2-DMN, 1,3-DMN, 1,4-DMN, 1,5-DMN, 1,6-DMN, 1,7-DMN, 1,8-DMN, α-ethylnaphthalene and β-ethylnaphthalene. The feed material may further contain recycled desorbent and one or more of hydrocarbon compounds having a boiling point in the range of 220° to 270° C., such as α-methylnaphthalene β-methylnaphthalene, biphenyl, alkanes, cycloalkanes, alkenes and cycloalkenes. Industrially produced 2,6-DMN is typically contained in the feed material at a concentration of 5 to 55 wt%, mostly in the range of 8 to 40 wt%. If a feed material containing 2,6-DMN at a concentration of 40 wt% or higher is available, such a material may also be used in a process of the present invention.

In accordance with the method of the present invention, 2,6-DMN of high purity can be separated in high yield and in an industrially advantageous manner from a feed material containing a mixture of DMN isomers.

The following examples are provided for the purpose of further illustrating the present invention. It should, however, be noted that the present invention is by no means limited to these examples and that various modifications can be made without departing from the spirit of the invention. Unless otherwise noted, all parts and percents appearing in the following examples are on a weight basis.

Separation Factor

The adsorption characteristic, i.e., adsorption capacity, selectivity and desorption rate, of various adsorbents and desorbents as applied to a feed containing a mixture of DMN isomers can be measured with a dynamic testing apparatus. The apparatus is of a stainless steel column having an inside diameter of 8 mm and a length of 1 m. It is provided with a heat-insulating jacket. The column inlet is equipped with a distributor that ensures uniform liquid distribution to prevent channeling. Using this apparatus, a pulse test is conducted according to the standard procedures to be outlined below for obtaining selectivity and other data for various adsorbent/desorbent systems. The column is first packed with an adsorbent and conditioned by passage of a desorbent. Then, a feed containing a mixture of DMN isomers is injected in a pulse. When a predetermined amount of the feed has been introduced into the column, the apparatus is switched for the desorbent stream and the desorbent is permitted to flow in an amount within the range that maintains a plug flow without causing back mixing, thereby ensuring that the feed is uniformly distributed in the column. The column outlet is provided with a sampling port from which predetermined amounts of effluents are periodically sampled and analyzed by gas chromatography for determining the quantities of individual components in each fraction. By plotting the concentrations of individual components against elution times, peak envelopes for the respective components can be constructed.

The separability of an adsorbent is generally indicated by the separation factor K which is defined as the concentration ratio of two components of interest in the adsorbent phase, divided by the concentration ratio of the same components in the fluid phase when they are in adsorption equilibrium. If the concentrations of components A and B in the adsorbent phase are denoted by $X_A$ and $X_B$, respectively, with the volume percents of the same components in the adsorbent phase denoted by $Y_A$ and $Y_B$, respectively, the separation factor $K_A{}^B$ for components A and B is expressed as:

$$K_A{}^B = \frac{Y_B/Y_A}{X_B/X_A}$$

The two components are said to be "in adsorption equilibrium" when no net mass transfer will take place between the fluid and adsorbent phases. If component B is supposed to have greater adsorption affinity power than component A, the separability of an adsorbent can be evaluated by the magnitude of $K_A{}^B$. Stated more specifically, if the value of $K_A{}^B$ is close to 1.0, selective adsorption of component B over A will not take place and the adsorbent will adsorb the two components to substantially the same degree. If the value of $K_A{}^B$ exceeds 1.0, component B will be preferentially adsorbed over component A.

The separation factor $K_A{}^B$ may be expressed as $K_A/K_B$, where $K_A$ is the volume index of component A and $K_B$ is the volume index of component B.

The volume index can be determined by measuring the distance from the time distance between a summit of the peak envelope for adsorbed component and a known reference point. The volume index in this sense is expressed by the volume of a desorbent that has been charged until the peak time is reached. The known reference point is determined in terms of the volume of the charged desorbent. The "void volume" or the volume of voids between adsorbent particles in the column, namely, the volume permeated by a tracer component which does not take part in adsorption, can be determined by measuring the physical properties of the adsorbent, such as its true density and the pore volume, and its packing density in the column. The "known reference point" is defined as the time calculated by dividing the so-determined "void volume" by the volume of desorbent charged.

Therefore, for the purposes of the present invention, the value of separation factor $K_{2,6}{}^i$ of a certain component i with respect to 2,6-DMN can be expressed as the ratio of the distance with respect to time between the summit of the peak envelope for component i and the reference point, to the distance between the summit of the peak envelope for 2,6-DMN and the reference point. In accordance with the method of the present invention, the separation factor, $K_{2,6}{}^i$, of a certain DMN isomer i with respect to 2,6-DMN is greater than unity for all DMN isomers other than 2,6-DMN and this clearly indicates the possibility of selectively separating 2,6-DMN from other DMN isomers.

REFERENTIAL EXAMPLE 1

Adsorption Separation

Granules (size distribution: 250–420 μm) of zeolite Y having lithium on cation sites which was prepared by ion-exchanging a sodium on the zeolite Y with lithium in 70.7% of ion-exchange rate, were packed in a stainless steel column (i.d., 8 mm; length, 1 m) equipped with a heat-insulating jacket. The column inlet was equipped with a distributor to ensure that a liquid feed would be uniformly distributed to prevent channeling. With the column temperature held at 100° C., paraxylene as a desorbent was supplied at one end of the column at a rate of 5 ml/min for its conditioning (i.e., the column was filled with the desorbent). A feed material containing a mixture of DMN isomers (for their names and proportions, see Table 1) was supplied into the column from its top in pulsive amounts of 3 ml. The column operation was switched for a desorbent stream and the desorbent was supplied at a rate of 0.4 ml/min so as to distribute the feed uniformly in the column. The effluents coming out of the outlet of the column were sampled at predetermined intervals, with the time at which elution with the desorbent started being taken as time zero. The quantities of the components in the individual fractions were determined by gas chromatography and the changes in the concentrations of the components in each fraction as against the elution time were measured. Peak envelopes were constructed by plotting the values of analysis for individual fractions. The results are shown in Table 2.

REFERENTIAL EXAMPLES 2 AND 3

Adsorption Separation

The procedure of Referential Example 1 were repeated except that the lithium-exchanged zeolite Y was replaced by two different species of zeolite Y that were ion-exchanged with sodium and zinc, respectively. The results are shown in Table 2.

REFERENTIAL EXAMPLE 4

Adsorption Separation

The procedures of Referential Example 2 were repeated except that toluene was used as a desorbent. The results are shown in Table 2.

TABLE 1

| Component | 2,6-DMN | 2,7-DMN | 1,6-DMN | 2,3-DMN | 1,3/1,4/1,5-DMN | 1,7/1,8-DMN | Others |
|---|---|---|---|---|---|---|---|
| Proportion (%) | 8.9 | 10.4 | 7.7 | 3.7 | 9.2 | 9.0 | 51.1 |

TABLE 2

| Referential Example No. | Adsorbent | Desorbent | Separation factor $K_{2,6}^i$ (component i) | | | | | | | | |
| | | | 2,7 | 2,3 | 1,2 | 1,3 | 1,4 | 1,5 | 1,6 | 1,7 | 1,8 |
|---|---|---|---|---|---|---|---|---|---|---|---|
| 1 | Li—Y | paraxylene | 2.00 | 1.67 | 1.74 | 1.74 | 1.74 | 1.74 | 1.86 | 1.91 | 1.91 |
| 2 | Na—Y | paraxylene | 1.90 | 1.62 | 0.93 | 0.93 | 0.93 | 0.93 | 1.61 | 1.14 | 1.14 |
| 3 | Zn—Y | paraxylene | 1.47 | 1.81 | 1.35 | 1.58 | 1.58 | 1.58 | 1.61 | 2.68 | 2.68 |
| 4 | Na—Y | toluene | 1.92 | 1.03 | 0.85 | 0.76 | 0.76 | 0.76 | 0.94 | 0.88 | 0.88 |

In the following Examples the adsorption separation was carried out in a simulated moving bed.

The adsorption separation using the simulated moving bed has been well known in the art since it was taught by U.S. Pat. No. 2,985,589 and Japanese patent publication No. 15681/1967. For example, a separation of fructose from glucose using the simulated moving bed is disclosed in U.S. Pat. No. 4,182,633 and Japanese patent application (OPI) No. 102288/1979 (the term "OPI" as used herein refers to a "published unexamined Japanese patent application"). The process comprises continuously chromatographically separating a feed material containing a mixture of DMN isomers into a solution of 2,6-DMN isomers, which is adsorbable component, and a solution mainly containing 2,6-DMN which is non-adsorbable component, with a desorbent. The apparatus comprises a bed packed with a zeolite, a fluid conduit interconnecting the upstream end and downstream end of the bed to form a loop through which a fluid is passed in one direction, and a plurality of zones which perform as an inlet for a desorbent, an outlet for a sorbed component, an inlet for a feed material and outlet for a non-sorbed component in turn at the selected position in the bed in the fluid flow direction; and the apparatus is operated by shifting the positions of said inlet and outlets to those provided downstream at a predetermined time interval. Thus, these zones composed of four zones which comprise an adsorbing zone from an inlet for a feed material to an outlet for a non-sorbed component; a refining zone from an outlet of a non-sorbed component to an inlet for an adsorbent; a desorbing zone from an inlet for an adsorbent to an outlet for sorbed component; and a concentrating zone from an outlet for sorbed component to an inlet for a feed material.

EXAMPLE 1

Adsorption Separation

Twelve stainless steel columns (i.d., 18 mm; length, 416 mm) packed with granules of lithium zeolite Y having a size distribution of 250–420 μm in diameter were used to effect adsorption separation of 2,6-DMN from a feed material having the composition shown in Table 3. The operation temperature was 100° C. Paraxylene was used as a desorbent. The feed material and the desorbent were supplied into the column at their respective inlets at a rates of 111 ml/hr and 366 ml/hr. The product stream, or a solution containing the enriched 2,6-DMN, came out of the column at a rate of 84 ml/hr while the by-product stream, or a raffinate, came out at a rate of 393 ml/hr. The distribution of concentrations in the system reached a steady state in 19 hours after the start of introduction of the feed material and the desorbent. The analytical results of the product stream are shown in Table 4. The purity of the product stream was found to be of 70.0% 2,6-DMN. Paraxylene can be readily removed from the product stream by distillation, so it can be said that the purity of 2,6-DMN was markedly increased from 13.4% to 70.0%. The recovery of 2,6-DMN by adsorption separation was calculated to be 72.3%.

Separation by Crystallization

A portion (133.0 g) of the product stream was charged into an agitation vessel (diameter, 80 mm; capacity, 300 ml) equipped with a glass jacket. A coolant that was program-controlled for its temperature was passed through the jacket at a stirring rate of 50 rpm so that the solution was cooled from 21.8° C. to 7.1° C. over a period of 94 minutes for effecting crystallization. The resulting crystal was filtered through a filter cloth of 200 mesh and recovered. The mother liquor wetting the recovered crystal was removed with a centrifuge and the crystal was subsequently washed with small amount of methanol and dried under vacuum. The purified crystal weighed 4.86 g and its composition analyzed to be 99.81% 2,6-DMN, 0.13% 2,7-DMN, and the balance being 0.06%. The recovery of 2,6-DMN in the crystallization operation was calculated to be 22.3% and the overall yield of 2,6-DMN obtained by the sequence of adsorption separation and crystallization was calculated to be 16.5%.

EXAMPLE 2

Adsorption Separation

Adsorption separation of 2,6-DMN from a feed material having the same composition as used in Example 1 was conducted under the same conditions as in Example 1 except that orthoxylene was used as a desorbent. The distribution of concentrations in the system reached a steady state in 21 hours after the start of the introduction of the feed material and the desorbent. The analytical results of analysis of the product stream are shown in Table 4. The purity of the product stream was found to be of 72.6% 2,6-DMN. The recovery of 2,6-DMN was calculated to be 70.0%.

Separation by Crystallization

A portion (125.0 g) of the product stream was subjected to separation by crystallization as in Example 1 except that the solution was cooled from 20.5° C. to 5.0° C. over a period of 90 minutes. The purified crystal weighed 9.03 g and its composition analyzed to be 99.10% 2,6-DMN, 0.11% 2,7-DMN and the balance being 0.79%. The recovery of 2,6-DMN by crystallization was calculated to be 50.4% and the overall yield of 2,6-DMN obtained by the sequence of adsorption separation and crystallization was calculated to be 35.3%.

EXAMPLE 3

Adsorption Separation

Adsorption separation of 2,6-DMN from a feed material having the same composition as used in Example 1 was conducted under the same conditions as in Example 1 except that a mixture consisting of orthoxylene and paraxylene at a weight ratio of 50:50 was used as a desorbent. The distribution of concentrations in the system reached a steady state in 21 hours after the start of the introduction of the feed material and the desorbent. The analytical results of the product stream are shown in Table 4. The purity of the product stream was found to be of 73.2% 2,6-DMN. The recovery of 2,6-DMN was calculated to be 74.0%.

Separation by Crystallization

A portion (125.2 g) of the product stream was subjected to separation by crystallization as in Example 1 except that the solution was cooled from 20.3° C. to 5.1° C. over a period of 90 minutes. The purified crystal weighed 7.94 g and its composition was analyzed to be 99.37% 26-DMN, 0.13% 2,7-DMN and the balance being 0.5%. The recovery of 2,6-DMN by crystallization was calculated to be 42.0% and the overall yield of 2,6-DMN obtained by the sequence of adsorption separation and crystallization was calculated to be 31.1%.

EXAMPLE 4

Adsorption Separation

Adsorption separation of 2,6-DMN from a feed material having the same composition as used in Example 1 was conducted under the same conditions as in Example 1 except that a mixture consisting of orthoxylene, paraxylene and naphthalene at a weight ratio of 40:40:20 was used as a desorbent. The distribution of concentrations in the system reached a steady state in 24 hours after the start of the introduction of the feed material and the desorbent. The analytical results of the product stream are shown in Table 3. The purity of the product stream was found to be of 61.9% 2,6-DMN. The recovery of 2,6-DMN was calculated to be 65.0%.

Separation by Crystallization

A portion (125.3 g) of the product stream was subjected to separation by crystallization as in Example 1 except that the solution was cooled from 35.0° C. to 6.2°

C. over a period of 175 minutes. The purified crystal weighed 3.88 g and its composition was analyzed to be 99.03% 2,6-DMN, 0.23% 2,7-DMN and the balance being 0.74%. The recovery of 2,6-DMN by crystallization was calculated to be 23.0% and the overall yield of 2,6-DMN obtained by the sequence of adsorption separation and crystallization was calculated to be 14.2%.

EXAMPLE 5

Adsorption Separation

Adsorption separation of 2,6-DMN from a feed material having the same composition as used in Example 1 was conducted under the same conditions as in Example 1 except that a mixture of paraxylene and cyclopentane at a weight ratio of 60:40 was used as a desorbent. The distribution of concentrations in the system reached a steady state in 21 hours after the start of the introduction of the feed material and the desorbent. The analytical results of the product stream are shown in Table 4. The purity of the product stream was found to be of 60.9% 2,6-DMN. The recovery of 2,6-DMN was calculated to be 66.0%.

Separation by Crystallization

A portion (125.5 g) of the product stream was subjected to separation by crystallization as in Example 1 except that the solution was cooled from 20° C. to 51.1° C. over a period of 90 minutes. The purified crystal weighed 3.48 g and its composition was analyzed to be 99.05% 2,6-DMN, 0.29% 2,7-DMN and the balance being 0.64%. The recovery of 2,6-DMN by crystallization was calculated to 20.5% and the overall yield of 2,6-DMN obtained by the sequence of adsorption separation and crystallization was calculated to be 15.2%.

COMPARATIVE EXAMPLE 1

Adsorption Separation

Adsorption separation of 2,6-DMN from a feed material having the composition shown in Table 5 was conducted under the same conditions as employed in Example 1 except that toluene was used as a desorbent. The distribution of concentrations in the system reached a steady state in 21 hours after the start of the introduction of the feed material and the desorbent. The analytical results of the product stream are shown in Table 4. The purity of the product stream was found to contain 45.4% 2,6-DMN. The product stream contained a considerable amount of 2,7-DMN as compared with 2,6-DMN. This fact, taken in conjunction with the low concentration of 2,6-DMN (45.4%), led to the conclusion that the composition of the product stream was not favorable for ensuring the high recovery of 2,6-DMN by subsequent crystallization. In other words, the use of toluene as a desorbent was found to be already undesirable in the step of adsorption separation.

COMPARATIVE EXAMPLE 2

Adsorption Separation

Adsorption separation of 2,6-DMN from a feed material having the same composition as used in Example 1 was conducted under the same conditions as in Example 1 except that a mixture of paraxylene and naphthalene at a weight ratio of 50:50 was used as a desorbent. The distribution of concentrations in the system reached a steady state in 21 hours after the start of the introduction of the feed material and the desorbent. The product stream obtained was analyzed to consist of 88.6% of paraxylene and naphthalene, 5.3% of 2,6-DMN, 0.8% of 2,7-DMN, 0.4% of 2,3-DMN, and 4.9% of the other components. The purity of the product stream was found to contain 46.5% 2,6-DMN. It is clearly evident from these results that the purity of 2,6-DMN in the product stream obtained by using paraxylene and naphthalene as desorbent components was too low to warrant a high recovery of 2,6-DMN by subsequent crystallization. In other words, the use of these desorbent components was found to be already undesirable in the step of adsorption separation.

EXAMPLE 6

Adsorption Separation

Twelve stainless steel columns (i.d., 18 mm; length, 416 mm) each packed with lithium zeolite Y in the upper layer (81 vol%) and sodium zeolite X in the lower layer (19 vol%) were used to effect adsorption separation of 2,6-DMN at 100° C. from a feed material having the composition shown in Table 6. Paraxylene was used as a desorbent. The feed material and the desorbent were supplied into the column at their respective inlets at rates of 108 ml/hr and 270 ml/hr. The product stream and the by-product stream cane out of the column at respective states of 65 ml/hr and 313 ml/hr. The distribution of concentrations in the system reached a steady state in 20 hours after the start of the introduction of the feed material and the desorbent. The results of analysis of the product stream are shown in Table 4. The purity of the product stream was found to contain 80.8% 2,6-DMN. The recovery of 2,6-DMN by adsorption separation was calculated to be 71.2%.

TABLE 3

| Component | 2,6-DMN | 2,7-DMN | 2,3-DMN | 1,7-DMN | 1,6/1,2-DMN | 1,3/1,4/1,5/1,8-DMN | Others |
|---|---|---|---|---|---|---|---|
| Composition (%) | 13.4 | 13.5 | 4.5 | 14.7 | 19.0 | 29.9 | 5.0 |

TABLE 4

| Run No. | Zeolite type | Desorbent (weight ratio) | Composition of the product stream (%) | | | | |
|---|---|---|---|---|---|---|---|
| | | | desorbent | 2,6-DMN | 2,7-DMN | 2,3-DMN | Others |
| Example 1 | Li—Y | paraxylene | 78.8 | 14.8 | 0.2 | 0.1 | 6.1 |
| Example 2 | Li—Y | orthoxylene | 80.3 | 14.2 | 0.8 | 0.1 | 4.6 |
| Example 3 | Li—Y | orthoxylene/paraxylene (50/50) | 79.5 | 15.0 | 0.6 | 0.2 | 4.7 |
| Example 4 | Li—Y | orthoxylene/paraxylene/ | 78.5 | 13.3 | 0.3 | 0.2 | 7.7 |

TABLE 4-continued

| Run No. | Zeolite type | Desorbent (weight ratio) | Composition of the product stream (%) | | | | |
|---|---|---|---|---|---|---|---|
| | | | desorbent | 2,6-DMN | 2,7-DMN | 2,3-DMN | Others |
| Example 5 | Li—Y | naphthalene (40/40/20) paraxylene/ cyclopentane (60/40) | 78.0 | 13.4 | 0.4 | 0.3 | 7.9 |
| Example 6 | Li—Y/ Na—X (1/1) | paraxylene | 78.6 | 17.3 | 0.5 | 0.1 | 3.5 |
| Comparative Example 1 | Li—Y | toluene | 87.0 | 5.9 | 1.3 | 0.6 | 5.2 |
| Comparative Example 2 | Li—Y | paraxylene/ naphthalene (50/50) | 88.6 | 5.3 | 0.8 | 0.4 | 4.9 |

TABLE 5

| Component | 2,6-DMN | 2,7-DMN | 2,3-DMN | 1,7-DMN | Others |
|---|---|---|---|---|---|
| Proportion (%) | 13.6 | 16.1 | 3.2 | 15.0 | 52.1 |

TABLE 6

| Component | 2,6-DMN | 2,7-DMN | 2,3-DMN | 1,7-DMN | Others |
|---|---|---|---|---|---|
| Proportion (%) | 12.7 | 16.9 | 3.7 | 15.6 | 51.1 |

Separation by Crystallization

A portion (121.3 g) of the product stream was subjected to crystallization as in Example 1. The purified crystal weighed 9.30 g and its composition was analyzed to be 99.57% 2,6-DMN, 0.38% 2,7-DMN and the remainder being 0.05%. The recovery of 2,6-DMN by crystallization was calculated to be 44.2% and the overall yield of 2,6-DMN obtained by the sequence of adsorption separation and crystallization was calculated to be 31.5%.

REFERENTIAL EXAMPLE 5

Separation by Crystallization

An agitation vessel of the same type as used in the crystallizing steps of Example 1 was charged with 152.2 g of a solution consisting of 2,6-DMN, 2,7-DMN and paraxylene at a weight ratio of 9:9:82 and the charged solution was cooled from 19.5° C. to 7.0° C. over a period of 72 minutes. The change in the composition of the liquid phase in the solution with time was analyzed and it was found that 2,6-DMN and 2,7-DMN formed a eutectic mixture at a 2,6-DMN/2,7-DMN ratio of 0.59.

REFERENTIAL EXAMPLE 6

Separation by Crystallization

An agitation vessel of the same type as used in hte crystallizing step of Example 1 was charged with 150.6 g of a solution consisting of 2,6-DMN, 2,7-DMN and paraxylene at a weight ratio of 30:30:40 and the charged solution was cooled from 18.2° C. to 7.1° C. over a period of 65 minutes. The change in the composition of the liquid phase in the solution with time was analyzed and it was found that 2,6-DMN and 2,7-DMN formed a eutectic mixture at a 2,6-DMN/2,7-DMN ratio of 0.67.

In a two-component system, 2,6-DMN and 2,7-DMN will theoretically form a eutectic at a 2,6-DMN/2,7-DMN ratio of 0.71. Therefore, the results in Referential Examples 5 and 6 clearly show that the eutectic ratio of 2,6-DMN to 2,7-DMN decreased in the presence of paraxylene; in other words, even if the two DMN isomers are present in a solution to be crystallized, a greater amount of 2,6-DMN can be obtained before a eutectic mixture with 2,7-DMN starts to form in the presence of paraxylene than in its absence.

That is to say, if the concentration of 2,6-DMN is much higher than that of 2,7-DMN in a mixture, a greater amount of 2,6-DMN can be recovered before starting to form a eutectic mixture provided that a paraxylene is present.

While the invention has been described in detail and with reference to specific embodiments thereof, it will be apparent to one skilled in the art that various changes and modifications can be made therein without departing from the spirit and scope thereof.

What is claimed is:

1. A method of separating 2,6-dimethylnaphthalene from a feed material consisting essentially of a mixture of dimethylnaphthalene isomers comprising
   adsorption separation using an adsorbent of a zeolite Y containing alkali metal or zinc and a desorbent of an organic solvent consisting essentially of paraxylene and/or orthoxylene to obtain a solution consisting of the desorbent and the feed material wherein 2,6-dimethylnaphthalene comprises at least 60 wt% of said mixture of dimethylnaphthalene isomers, and
   crystallization of said solution, said desorbent comprising between 30 to 90 wt% of the total weight of said solution, to obtain 2,6-dimethylnaphthalene of high purity in a crystalline form.

2. A method according to claim 1, wherein a zeolite Y contains lithium.

3. A method according to claim 1, wherein the concentration of paraxylene and/or orthoxylene in the desorbent is at least 70 wt%.

4. A method according to claim 1, wherein a zeolite Y contains lithium and the organic solvent is paraxylene.

5. A method according to claim 1, wherein the absorbent comprises in combination of a zeolite Y containing an alkali metal or zinc and a zeolite X containing an alkali metal.

6. A method according to claim 5, wherein the zeolite Y is positioned upstream and the zeolite X positioned downstream of supply of the feed material containing a mixture of dimethylnaphthalene isomers.

7. A method according to claim 5, wherein the adsorbent comprises a combination of a zeolite Y containing lithium and a zeolite X containing sodium.

8. A method according to claim 6, wherein the adsorbent comprises a combination of a zeolite Y containing lithium and a zeolite X containing sodium.

9. A method according to claim 1, wherein the crystallization comprises cooling the solution.

10. A method according to claim 1, wherein the crystallization comprises evaporating the desorbent from the solution.

11. A method according to claim 1, wherein the crystallization comprises adding one or more lower aliphatic alcohol to the solution.

12. A method according to claim 1, wherein the feed material contains 2,6-dimethylnaphthalene at a concentration of 5 to 40 wt% on feed material containing no desorbent.

13. A method according to claim 1, wherein the zeolite Y is ion-exchanged with an alkali metal or zinc at cation site thereof.

14. A method according to claim 5, wherein the zeolite Y is ion-exchanged with an alkali metal or zinc at a cation site thereof, and the zeolite X is ion-exchanged with an alkali metal at a cation site thereof.

* * * * *